US012759971B2

(12) United States Patent
Wen et al.

(10) Patent No.: US 12,759,971 B2
(45) **Date of Patent: *Oct. 13, 2026**

(54) ACETONITRILE PURIFICATION PROCESS FOR ULTRAHIGH PERFORMANCE LIQUID CHROMATOGRAPHY-MASS SPECTROMETER

(71) Applicant: FTSCI (HUBEI) SCIENCE AND TECHNOLOGY CO., LTD, Wuhan (CN)

(72) Inventors: Sheng Wen, Wuhan (AR); ZhengChong Zhao, Wuhan (CN); ChunLi Gong, Wuhan (CN); Fan Cheng, Wuhan (CN); Hai Liu, Wuhan (CN); FuQiang Hu, Wuhan (CN)

(73) Assignee: FTSCI (HUBEI) SCIENCE AND TECHNOLOGY CO., LTD, Wuhan (CN)

(*) Notice: Subject to any disclaimer, the term of this patent is extended or adjusted under 35 U.S.C. 154(b) by 986 days.

This patent is subject to a terminal disclaimer.

(21) Appl. No.: 17/307,153

(22) PCT Filed: Apr. 16, 2020

(86) PCT No.: PCT/CN2020/085151

§ 371 (c)(1),
(2) Date: Feb. 28, 2023

(87) PCT Pub. No.: WO2021/208023

PCT Pub. Date: Oct. 21, 2021

(65) Prior Publication Data

US 2023/0257340 A1 Aug. 17, 2023

(30) Foreign Application Priority Data

Apr. 14, 2020 (CN) ........................ 202010288491.X

(51) Int. Cl.
*C07C 253/34* (2006.01)
*G01N 30/72* (2006.01)

(52) U.S. Cl.
CPC ........ *C07C 253/34* (2013.01); *G01N 30/7233* (2013.01)

(58) Field of Classification Search
CPC .......................... C07C 253/34; G01N 30/7233
See application file for complete search history.

(56) References Cited

FOREIGN PATENT DOCUMENTS

| | | |
|---|---|---|
| CN | 102775327 A | 11/2012 |
| CN | 107382776 A | 11/2017 |

OTHER PUBLICATIONS

Root et al. Waters Corporation. Increasing Sample Throughput Using the AQUITY UPLC System with 2D Technology and Parallel Column Regeneration. 2013 (Year: 2013).*

* cited by examiner

*Primary Examiner* — Clinton A Brooks
*Assistant Examiner* — Jerica Katlynn Wilson
(74) *Attorney, Agent, or Firm* — Jose Cherson Weissbrot

(57) ABSTRACT

The present invention relates to the technical field of acetonitrile refining, and in particular, to an acetonitrile purification process for an ultrahigh performance liquid chromatography-mass spectrometer. According to the acetonitrile purification process provided by the present invention, the production cost may be reduced and the yield may be increased to reach 95% or more while the quality of the chromatographic pure acetonitrile is further improved to reach the UPLC-MS level; and an industrial UPLC-MS level acetonitrile purification and preparation method provided by the present invention has the advantages of simple operation, low cost, safety, high efficiency and capability of realizing large-scale industrial production.

4 Claims, 2 Drawing Sheets

ACETONITRILE PURIFICATION PROCESS FOR ULTRAHIGH PERFORMANCE LIQUID CHROMATOGRAPHY-MASS SPECTROMETER

TECHNICAL FIELD

The present invention relates to the technical field of acetonitrile refining, and in particular, to an acetonitrile purification process for an ultrahigh performance liquid chromatography-mass spectrometer.

BACKGROUND

The ultrahigh performance liquid chromatography-mass spectrometer (UPLC-MS) segment generally refers to a chromatographic special solvent or reagent, has high ultraviolet transmittance at the low wavelength position, and has strict and harsh requirements on indexes such as acidity, alkalinity, evaporation residues, metal ions, water and the like, some of which are required so reach ppb grade, even some of which are required to reach ppt grade. The UPLC-MS reagent refers to a standard reagent used during ultrahigh performance liquid chromatography-mass spectrometry. Under the chromatographic condition, only the peaks of specified compounds appear, the peaks of impurities cannot appear, or the peak of background noise is required to be lower than the sensitivity of the instrument. The UPLC-MS reagent has high purity, and has high requirements on dust, water and metal ions in addition to the requirement on high content, thus belonging to the category of high-purity reagents. The UPLC-MS acetonitrile reagent is one of the commonly used liquid chromatography mobile phases. Its chromatographic pure market in China is mostly monopolized by foreign reagent companies, such as Merck, Sigma, Fisher, Tenia, etc., their products are expensive, which will lead to excessive cost consumption relative to the chromatographic pure users.

At present, a variety of acetonitrile purification processes have been reported at home and abroad. The main purification method includes: oxidation, dehydrogenation, heavy component removal, adsorption and rectification, or combination of oxidation, dehydrogenation, heavy component removal, decoloration/adsorption-rectification, and has the disadvantages of low yield, or low purity resulting high cost, or no capability of meeting the scientific research requirements on the indexes such as water, evaporation residues, metal ions, fluorescence, etc. Therefore, reducing the production cost and improving the quality of the UPLC-MS acetonitrile reagent need to be further explored and improved.

SUMMARY

To solve the above problem, a first aspect of the present invention provides an acetonitrile purification process, including the following steps:

oxidation: feeding industrial acetonitrile into a reaction kettle through a raw material pump, adding a catalyst in the reaction kettle, heating the reaction kettle after reacting for 1 to 6 h under the conditions of 80 to 90° C. and 10 to 90 kPa, and condensing the obtained gas by a condenser to enter an intermediate buffer tank to obtain an oxidized material;

adsorption: feeding the oxidized material into an adsorption column through a feeding pump and a flowmeter sequentially, and performing adsorption at a flow velocity of 0.01 to 2 m/s to obtain an absorbed material;

rectification: feeding the adsorbed material into a rectifying kettle, adding a drying agent into the rectifying kettle, heating the rectifying tower after reacting at 80 to 90° C. for 1 to 5 h, feeding gas generated in the rectifying tower into a rectifying tower to perform reflex for 2 to 10 h, extracting a tower top gas of the rectifying tower to sequentially pass through a reflux condenser and a reflux tank, and feeding the obtained reflux fluid into a finished product tank to obtain a semi-finished product; and filtration: filtering the semi-finished product to obtain acetonitrile for an ultrahigh performance liquid chromatography-mass spectrometer.

As a preferred technical solution of the present invention, the catalyst accounts for 0.01-5 wt % of the industrial acetonitrile.

As a preferred technical solution of the present invention, the adsorption column includes an online adsorption column and a regenerative activation column which are connected in parallel.

As a preferred technical solution of the present invention, the number of the regenerative activation columns is as same as that of the online adsorption columns, and the number of the online adsorption columns is selected from one of one, two, three, four and five.

As a preferred technical solution of the present invention, the flow of the reflux is 1 to 100 kg/h.

As a preferred technical solution of the present invention, the extracted flow is 1-30 kg/h, and the extracted reflux ratio is (1-2):1.

As a preferred technical solution of the present invention, in the rectification, the initially extracted reflux fluid of 1 to 5 h is removed, and the rest reflux fluid is fed into the finished product tank to obtain the semi-finished product.

As a preferred technical solution of the present invention, in the filtration, the finished product is sequentially filtered by a filter I, a filter II, a filter III, a filter IV, a filter V and a filter VI to obtain acetonitrile for the ultrahigh performance liquid chromatography-mass spectrometer.

As a preferred technical solution of the present invention, the type of a filter membrane of the filter is selected from two or more of a plastic filter membrane, an anionic filter membrane and a cationic filter membrane.

A second aspect of the present invention provides application of the acetonitrile purification process described above, wherein the acetonitrile purification process is applied to an ultrahigh performance liquid chromatography-mass spectrometer.

Compared with the prior art, the acetonitrile purification process provided by the present invention has the following beneficial effects: the production cost may be reduced and the yield may be increased to reach 95% or more while the quality of the chromatographic pure acetonitrile is further improved to reach the UPLC-MS grade; and an industrial UPLC-MS grade acetonitrile purification and preparation method provided by the present invention has the advantages of simple operation, low cost, safety, high efficiency and capability of realizing large-scale industrial production.

Figure 1:
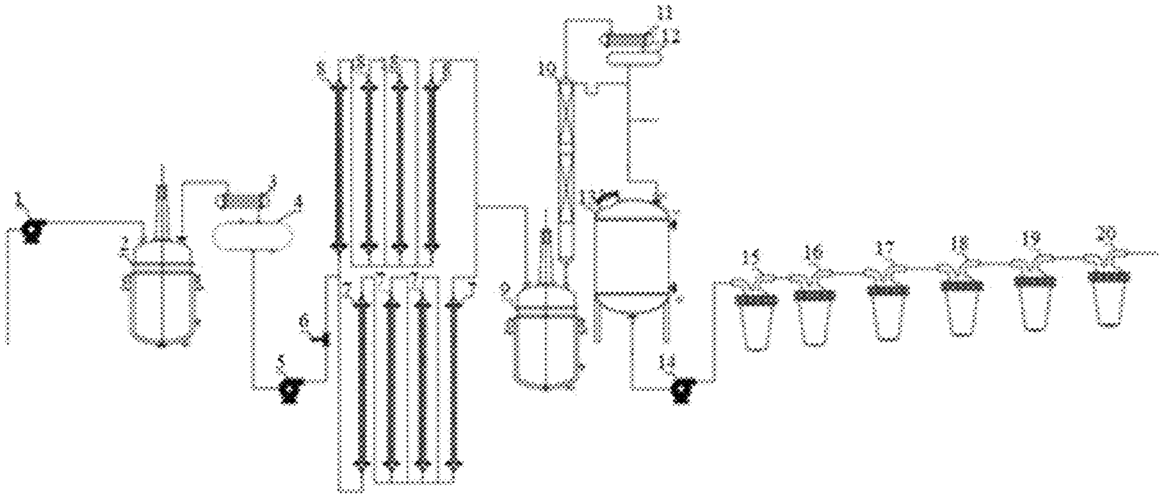
FIG. 1 is a device flowchart of an acetonitrile purification process for an ultrahigh performance liquid chromatography-mass spectrometer.

In the drawings, 1—raw material pump, 2—reaction kettle, 3—condenser, 4—intermediate buffer tank, 5—feeding pump, 6—flowmeter. 7—online adsorption column, 8—regenerative activation column, 9—rectifying kettle, 10—rectifying tower. 11—reflux condenser. 12—reflux tank, 13—finished product tank, 14—semi-finished product feeding pump, 15—filter I, 16—filter II, 17—filter III, 18—filter IV, 19—filter V, 20—filter VL.

DETAILED DESCRIPTION OF THE EMBODIMENTS

The contents of the present invention may be understood more easily with reference to the following detailed description of the preferred implementation methods of the present invention and the included embodiments. Unless otherwise defined, all technical and scientific terms used herein have the same meanings as those generally understood by a person of ordinary skill in the art to which the present invention belongs. In case of contradiction, the definition in this specification shall prevail.

As used herein, the term “prepared from” is synonymous with “comprising”. The terms “including”. “comprising”, “having”, “containing” or any other variations thereof used herein are intended to cover non-exclusive inclusion. For example, a composition, step, method, product or device including the listed elements are unnecessarily only limited to those elements, and may include other elements that are not explicitly listed, or elements inherent to the composition, step, method, product or device.

The conjunction “consisting of” excludes any unspecified elements, steps or components. If used in the claims, the phrase will make the claims closed, such that the claims do not contain materials other than those described, except conventional impurities related to the claims. When the phrase “consisting of” appears in the clause of the main body of the claims instead of immediately following the subject, the phrase only limits the elements described in the clause, and other elements are not excluded from the claims as a whole.

When equivalent, concentration, or other values or parameters are expressed in a range, a preferred range, or a range defined by a series of upper and lower limit preferred values, this should be understood as specifically disclosing all ranges formed by any pair of upper limit or preferred values in any range and lower limit or preferred values in any range, regardless of whether the range is separately disclosed. For example, when the range “1 to 5” is disclosed, the described range should be interpreted as including the ranges “1 to 4”, “1 to 3”, “1 to 2”, “1 to 2 and 4 to 5”, “1 to 3 and 5”, etc. When a numerical value is described herein, unless otherwise specified, the range is intended to include its end value and all integers and fractions within the range.

The singular form includes a plural discussion object, unless the context clearly indicates otherwise. “Optional” or “any one” means that items or events described below may or may not occur, and the description includes the situation where the event occurs and the situation where the event does not occur.

Approximate terms in the description and the claims is used to modify a quantity, indicating that the present invention is not limited to the specific quantity, and may include modified parts that are close to the quantity, acceptable, and do not lead to change of related basic functions. Accordingly, the use of “about” or the like modifying a numerical value means that the present invention is not limited to the precise numerical value. In some examples, the approximate term may correspond to the accuracy of an instrument that measures a value. In the description and the claims of the present application, the range limitations may be combined and/or interchanged, and unless otherwise specified, these ranges include all subranges included therein.

In addition, the indefinite articles “a” and “an” before an element or component of the present invention have no limitation on the quantity requirements (that is, the occurrence number) of the element or component. Therefore, “a” or “an” should be interpreted as including one or at least one, and the element or component in the singular form also includes the plural form, unless the quantity is obviously intended to refer to the singular form.

The present invention will be described below by specific embodiments, but not limited to the specific embodiments given below.

A first aspect of the present invention provides an acetonitrile purification process, including the following steps:

oxidation: feeding industrial acetonitrile into a reaction kettle through a raw material pump, adding a catalyst in the reaction kettle, heating the reaction kettle after reacting for 1 to 6 h under the conditions of 80 to 90° C. and 10 to 90 kPa, and condensing the obtained gas by a condenser to enter an intermediate buffer tank to obtain an oxidized material;

adsorption: feeding the oxidized material into an adsorption column through a feeding pump and a flowmeter sequentially, and performing adsorption at a flow velocity of 0.01 to 2 m/s to obtain an absorbed material;

rectification: feeding the adsorbed material into a rectifying kettle, adding a drying agent into the rectifying kettle, heating the rectifying tower after reacting at 80 to 90° C. for 1 to 5 h, feeding gas generated in the rectifying tower into a rectifying tower to perform reflex for 2 to 10 h, extracting a tower top gas of the rectifying tower to sequentially pass through a reflux condenser and a reflux tank, and feeding the obtained reflux fluid into a finished product tank to obtain a semi-finished product; and filtration: filtering the semi-finished product to obtain acetonitrile for an ultrahigh performance liquid chromatography-mass spectrometer.

Oxidation

In an implementation manner, the catalyst of the present invention accounts for 0.01-5 wt % of the industrial acetonitrile; further, the catalyst of the present invention accounts for 0.1-5 wt % of the industrial acetonitrile; and further the catalyst of the present invention accounts for 0.1 wt % of the industrial acetonitrile.

Preferably, the catalyst of the invention is selected from one of sodium sulfate, potassium dichromate, potassium permanganate, potassium iodate, concentrated sulfuric acid, ozone and a potassium superoxide composite catalyst; further, the catalyst of the present invention is the potassium superoxide composite catalyst.

The potassium superoxide composite catalyst of the present invention is compound of potassium superoxide and alkali, and the alkali may be selected from one or more of potassium hydroxide, sodium hydroxide and lithium hydroxide. The preparation raw materials of the potassium superoxide composite catalyst are potassium superoxide, potassium hydroxide and sodium hydroxide with a weight ratio of 1:(4-6):(6-10). The preparation method of the potassium superoxide composite catalyst of the present invention is a well-known preparation method in the field, for example, the potassium superoxide composite catalyst is obtained by mixing the preparation raw materials of the potassium superoxide.

High-purity acetonitrile may serve as a mobile phase and other excellent stationary phases of high-performance liquid chromatography, and has more stringent requirements on the contents of impurities, including water, hydrocyanic acid, acrylonitrile, cis-butene nitrile, trans-butene nitrile, allyl alcohol, oxazole, etc., which are required to be below a lower standard. These impurities will generate ultraviolet absorption in the ultraviolet absorption spectrum of 190-300 nm, so the purity of the acetonitrile may be judged by the ultraviolet absorption spectrum.

Since the industrial acetonitrile contains many impurities with the similar polarity to the acetonitrile, which are difficult to be removed directly through selective adsorption or rectification, the applicant firstly utilized the strong oxidizing property of the catalyst to oxidize the impurities in the industrial acetonitrile into polar oxygen-containing impurities with high boiling point or substances with great polarity difference from the acetonitrile. The applicant found that when the potassium superoxide serves as the catalyst and the content of the catalyst and the distillation time are controlled, the impurities may be completely oxidized. However, if the catalyst is not properly selected, for example, the potassium permanganate is used or the content and the distillation time are high, new impurities may be generated, affecting the yield and purification. If the content of the catalyst is too low or the distillation time is short, the impurities cannot be completely oxidized, finally affecting the yield and the purity.

In an implementation manner, lining materials of the reaction kettle, the condenser and the intermediate buffer tank of the present invention are selected from one of polytetrafluoroethylene, enamel, graphene and graphite.

Adsorption

In an implementation manner, according to the present invention, the oxidized material was fed into an adsorption column through a feeding pump and a flowmeter sequentially, and adsorption was conducted for 24-36 h at a flow velocity of 0.01 to 2 m/s to obtain an absorbed material.

The flow velocity is the displacement of liquid within per unit time.

Preferably, the adsorption column of the present invention includes an online adsorption column and a regenerative activation column which are connected in parallel.

More preferably, according to the present invention, the number of the regenerative activation columns is as same as that of the online adsorption columns, and the number of the online adsorption columns is selected from one of one, two, three, four and live; and further, the number of the adsorption columns of the present invention is 4.

Further preferably, an adsorbent of the adsorption column of the present invention is selected from one or more of activated carbon, aluminum oxide and a molecular sieve; and further, the adsorbent of the present invention is the activated carbon.

The activated carbon is a solid substance with a porous structure, which is prepared from a carbon-containing material through high-temperature carbonization, activation and the like. The specific surface area of the activated carbon is very large, and the total surface area of the pore channel is up to 600-1700 $m^2/g$; the activated carbon has stable property and is not liable to react with other substances at normal temperature: the activated carbon has high mechanical strength and is easy to regenerate; and the activated carbon, serving as an adsorption medium, has the following characteristics of high specific surface area, developed micropores, wide pore diameter distribution range, many micropores capable of adsorbing various substances, favorable adsorption of low-concentration substances and gas with low boiling point, stable chemical property, complete insolubility to water and other solvents and capability of being regenerated at high temperature under the condition of limiting oxygen. Therefore, the activated carbon is widely applied in the fields of chemical industry; environmental protection, food and pharmacy, catalyst carriers, electrode materials, etc. There are many types of activated carbon, such as coal granular activated carbon, wood granular activated carbon, shell granular activated carbon and the like. The present invention does not specifically limit the types of the activated carbon. In an implementation manner, the activated carbon of the present invention is purchased from Shanghai Bilang Environmental Protection Technology Co., Ltd. (the screen size is 2 mm).

Further preferably, the screen size of the activated carbon of the present invention is 2-3 mm.

The screen size is the size of a screen which granules may pass through, and has a certain conversion relationship with the mesh number which refers to the density of the screen.

The applicant found that by selecting the appropriate adsorbent and the average grain diameter thereof and controlling the number of the adsorption columns and the circulation time, the purity may be improved while the yield is increased. This may be because when the activated carbon, especially the activated carbon with an average grain diameter of 2-3 mm, serves as the adsorbent, the large specific surface area and the microporous structure of the activated carbon are conducive to physical adsorption with the oxidized impurities such as carboxylic acid and amide at this time, and the active group on the large specific surface area is conducive to the occurrence of chemical adsorption; and when the flow rate is controlled at 0.1-2 m/s for cyclic adsorption for 24-36 hours, the effect of removing the impurities is the best. In addition, the applicant found that when the flow rate is too high or the cyclic adsorption time is too short, the contact time of the acetonitrile and the adsorption columns is shortened, the impurities in the acetonitrile cannot form adsorption equilibrium with the adsorbent, which has a great influence on the purity, and when the flow rate is too low, the adsorption efficiency is too low, which will increase energy consumption and reduce production efficiency.

In addition, the adsorbent in the adsorption column is liable to deactivate after working for a certain time, so it is necessary to change the adsorbent or regenerate the adsorbent. Changing the adsorbent not only will increase the cost, but also will generate solid waste to pollute the environment. If the adsorbent is regenerated at intervals, the production efficiency will be delayed. Therefore, the applicant has set up an online adsorption column and a regenerative activation column which are connected in parallel, and one of the online adsorption columns and the regenerative activation column is used for adsorption in the adsorption process. If the online adsorption column is used for adsorption, the online adsorption column may be replaced by the regenerative activation column after operation for a period of time, and the online adsorption column is regenerated, such that the production continuity may be ensured and the production efficiency is improved.

The regeneration method of the present invention is a well-known method in the field, for example, cleaning with ultrapure water and alkali firstly, washing with ultrapure water and finally performing thermal regeneration.

In an implementation manner, lining materials of the feeding pump, the flowmeter and the adsorption column of the present invention are selected from one of polytetrafluoroethylene, enamel, graphene and graphite.

Rectification

In an implementation manner, the drying agent of the present invention accounts for 0.01-5 wt % of the industrial acetonitrile; further, the drying agent of the present invention accounts for 0.1-5 wt % of the industrial acetonitrile; and further, the drying agent of the present invention accounts for 0.4 wt % of the industrial acetonitrile.

Preferably, the drying agent of the present invention is selected from one of silica gel, anhydrous calcium sulfate, calcium hydride, calcium chloride and phosphorus pentoxide; and further, the drying agent of the present invention is the phosphorus pentoxide.

More preferably, the flow of the reflux of the present invention is 1-100 kg/h. The flow of the present invention is a mass flow, which refers to the mass of fluid passing through the effective section of the closed pipeline or the open groove within per unit time.

Further preferably, according to the present invention, the extracted flow is 1-30 kg/h, and the extracted reflux ratio is (1-2):1.

The reflux ratio is a ratio of the flow L of the reflux fluid returning to the tower from the top of the distillation tower to the flow D of the product at the tower top during rectification operation, that is, $R=L/D$. The reflux ratio has an important influence on the separation effect and the economy of the rectification process.

Further preferably, in the rectification of the present invention, the initially extracted reflux fluid of 1 to 5 h is removed, and the rest reflux fluid is fed into the finished product tank to obtain the semi-finished product.

The applicant found that when the activated carbon is used for adsorption, a small amount of activated carbon impurities will be introduced, and the activated carbon is a non-polar adsorbent, so some polar impurities and water will remain. Therefore, the applicant adopted rectification operation and firstly used the drying agent to remove water from the intermediate material coming out of the adsorption column, and the applicant adopted phosphorus pentoxide with certain oxidation effect, which is beneficial to further oxidation of the impurities in the acetonitrile. After rectification was conducted under normal pressure for a period of time, the acetonitrile and other light component impurities were fed into the rectifying tower in the form of gas for reflux and extraction, heavy components were removed. By controlling the reflux flow and time, it may be ensured that the light component impurities were separated from the acetonitrile and were concentrated at the top of the rectifying tower. After reflux was conducted for a certain time, the gas is condensed and extracted at a certain flow. Furthermore, the applicant found that when the initial reflux of 1-5 h is removed, it is beneficial to improve the purity on the basis of ensuring the yield, which is mainly because there are more light component impurities in the initially extracted reflux fluid. Moreover, the applicant found that when the reflux or extracted flow is too high, the gathering degree of the light component impurities is low, the purity can be ensured when more reflux fluid is removed, and the efficiency is low when the reflux or extracted flow is too low. In addition, the applicant found that after the initially extracted reflux fluid of 1-5 h is removed by the method provided by the present invention, the purity is similar to the purity when more reflux fluid is removed, thereby ensuring large-scale production and now allowing to remove more reflux fluid.

In a preferred implementation manner, a filler of the rectifying tower of the present invention is a polytetrafluoroethylene regular filler.

In an implementation manner, lining materials of the rectifying kettle, the rectifying tower, the reflux condenser and the reflux tank of the present invention are selected from one of polytetrafluoroethylene, enamel, graphene and graphite.

Filtration

In an implementation manner, in the filtration of the present invention, the semi-finished product was filtered sequentially by a filter I, a filter II, a filter III, a filter IV, a filter V and a filter VI to obtain acetonitrile for an ultrahigh performance liquid chromatography-mass spectrometer: and further, in the filtration of the present invention, the semi-finished product was sequentially fed by the semi-finished product feeding pump into the filter I, the filter II, the filter III, the filter IV, the filter V and the filter VI to obtain the acetonitrile for the ultrahigh performance liquid chromatography-mass spectrometer. Preferably, the type of a filter membrane of the filter is selected from two or more of a plastic filter membrane, an anionic filter membrane and a cationic filter membrane. An example of a plastic filter membrane includes, but is not limited to a polytetrafluoroethylene filter membrane, a polypropylene filter membrane and a polyethylene filter membrane.

An example of an anionic filter membrane includes, but is not limited to a polytetrafluoroethylene anionic filter membrane, a polysulfone anionic filter membrane, a phenylate anionic filter membrane and a chitosan anionic filter membrane: in a preferred implementation manner, the anionic filter membrane is a polytetrafluoroethylene anionic filter membrane; and further, the polytetrafluoroethylene anionic filter membrane is purchased from Hangzhou Aier Environmental Protection Technology Co., Ltd.

The anionic filter membrane is a kind of macromolecular polymer membrane containing alkaline active groups and with high selective permeability to anions, also known as an ion selective permeability membrane. The anionic filter membrane consists of three parts: a polymer main chain with a fixed group, i.e., a macromolecular matrix, (also called as a basement membrane), a positively charged active group (i.e., cation), and an anion capable of moving freely on the active group. The essence of the anion exchange membrane is an alkaline electrolyte with selective permeability to anions, so the anion exchange membrane is also called as an ion selective permeability membrane. Generally, cations such as —$NH^{3+}$, —$NR_2H^+$ or —$PR^{3+}$ serve as active exchange groups, and OH— generated at the cathode serves as a carrier and moves to an anode through the selective permeability of the anion exchange membrane.

An example of a cationic filter membrane includes, but is not limited to a polytetrafluoroethylene sulfonated cationic filter membrane, a polysulfone sulfonated cationic filter membrane, a polyethylene sulfonated cationic filter membrane, a polyether sulfone sulfonated cationic filter membrane, a polyvinyl alcohol sulfonated cationic filter membrane and a polytetrafluoroethylene carboxylic cationic filter membrane; in a preferred implementation manner, the cationic filter membrane is the polytetrafluoroethylene sulfonated cationic filter membrane; and further, the polytetrafluoroethylene sulfonated cationic filter membrane of the present invention is purchased from Hangzhou Aier Environmental Protection Technology Co., Ltd.

The cationic filter membrane is a membrane with selectivity to cations, and has fixed groups and dissociable ions, for example, the sodium sulfonic acid type fixed group is sulfonate, and dissociated ions are sodium ions. The cation exchange membrane may be regarded as a macromolecular electrolyte. Since the cation membrane is negatively charged, the original dissociated positive ions are dissociated into water under the action of water molecules, but the positively charged cations may pass through the cation membrane after electrification outside the membrane through the effect of an electric field, and the anions cannot pass through due to homopolar repulsion, so the cation exchange membrane has selective permeability. The active groups of the cationic filter membrane mainly include a sulfonic acid group, a carboxyl group, a phosphate group, a phosphorus acid group, a phenolic group, an arsenic acid group and a selenic acid group, wherein the sulfonic acid membrane is a strong acid type ion exchange membrane, and others are of weak acid type.

More preferably, a filter membrane of the filter I of the present invention is a plastic filter membrane; and further, the filter membrane of the filter I of the present invention is a polytetrafluoroethylene filter membrane.

The polytetrafluoroethylene (PTFE) filter membrane is completely made of a natural and permanently hydrophobic PTFE material. Even if under very low-pressure difference, the polytetrafluoroethylene filter membrane can ensure the passage of moist air or other gases, but an aqueous solution cannot pass through the polytetrafluoroethylene filter membrane. The property of the polytetrafluoroethylene filter membrane is just opposite to that of a hydrophilic film. The PTEF filter membrane has extremely high chemical compatibility and almost can filter all organic solvents and strong corrosive chemicals.

Further preferably, a pore diameter of a filter membrane of the filter I of the present invention is 150-250 nm; further, the pore diameter of the filter membrane of the filter I of the present invention is 200 nm; and further, the filter membrane of the filter I is a polytetrafluoroethylene filter membrane which is purchased from Shanghai Bitai Biotechnology Co., Ltd. (the pore diameter is 200 nm).

The pore diameter refers to a shape and a size of a pore channel in porous solid. The pore is actually very irregular. The pore is generally regarded as a circle, and the size of the pore is represented by the radius of the pore. The pore diameter distribution is often related to the adsorption capability of the adsorbent and the activity of the catalyst.

Further preferably, filter membranes of the filter II and the filter III of the present invention are cationic filter membranes, and filter membranes of the filter IV and the filter V are anionic filter membranes.

As a preferred implementation manner, filter membranes of the filter II and the filter III of the present invention are anionic filter membranes, and filter membranes of the filter IV and the filter V are cationic filter membranes.

In a more preferred implementation manner, a filter membrane of the filter VI of the present invention is a plastic filter membrane: and further, the filter membrane of the filter VI of the present invention is a polytetrafluoroethylene filter membrane.

In a further preferred implementation manner, a pore diameter of a filter membrane of the filter VI of the present invention is 5-8 nm: further, the pore diameter of the filter membrane of the filter VI of the present invention is 7 nm; and further, the filter membrane of the filter VI is a polytetrafluoroethylene filter membrane, which is purchased from Shanghai Bitai Biotechnology Co., Ltd. (the pore diameter is 7 nm).

Through rectification operation, most impurities may be removed, but some impurities are difficult to remove by rectification, which may be the impurities with the boiling point close to that of the acetonitrile or forming an azeotrope, so the application performed filtration operation after rectification. Moreover, the applicant found that when the type and pore diameter of the filter membranes which sequentially pass through are controlled, the obtained acetonitrile may meet the requirement of the ultrahigh performance liquid chromatography-mass spectrometry, which is mainly achieved by firstly filtering impurities with large particles by a plastic filter membrane of 150-200 nm, further selectively filtering anions and cations by a cationic filter membrane and an anionic filter membrane and finally obtaining the final product by a plastic filter membrane with small pore diameter. Moreover, the applicant unexpectedly found that when polytetrafluoroethylene serves as a base material of the filter membrane, the purification effect is obviously improved, which may be because the polytetrafluoroethylene is a per fluorinated structure. Compared with the common carbon-hydrogen bond, the carbon-fluorine bond has smaller bond length and higher bond energy, the fluorine atom has more electronic structures and diameters than the hydrogen atom, thus being beneficial for the fluorine atom to cover the carbon-carbon main chain, improving the stability of the filter membrane and reducing the surface free energy of the filter membrane. When a semi-finished product is filtered, the semi-finished product is in contact with the fluorine atom covering the surface, the large charge and the low surface energy of the fluorine atom are beneficial to hindering the passage of the impurities. Furthermore, the characteristic of the polytetrafluoroethylene also endows the cationic and anionic filter membranes with higher selectivity and stability, and the ionic conductance of the material is increased, thus performing further purification.

Moreover, the applicant found that when a polytetrafluoroethylene sulfonated cationic membrane and a polytetrafluoroethylene anionic membrane are used, compared with other cationic membranes, plastic filter membranes and anionic membranes, the purification effect is higher, and when other cationic membranes, plastic filter membranes and anionic membranes are used, the purity of the acetonitrile may even be further reduced, which may be because the introduction of other impurities in the filtration process of other cationic membranes and anionic membranes.

In an implementation manner, lining materials of the filter I, the filter II, the filter III, the filter IV the filter V and the filter VI of the present invention are selected from one of polytetrafluoroethylene, enamel, graphene and graphite.

At present, most acetonitrile purification equipment is made of iron-containing materials such as carbon steel, stainless steel and the like. As the use time increases, it is prone to corrode to release metal ions such as iron ions, such that the metal ions such as iron are mixed into the acetonitrile and may react with the acetonitrile and impurities to affect the quality of the acetonitrile. The applicant may avoid the influence on the acetonitrile by the introduction of the metal ions by controlling materials of all devices of the present invention as the enamel or the polytetrafluoroethylene, thereby being beneficial to realizing large-scale production and ensuring the purity and yield of the final product.

According to the present invention, production is realized through the production sequence of oxidation, adsorption, rectification and filtration, and the production sequence cannot be changed at will. Firstly, the impurities are oxidized into substances with polarity greatly different from the acetonitrile before being selectively removed through adsorption and rectification, and new impurities may be generated due to the adsorbent in the adsorption process, so the new impurities in the adsorption process are removed through rectification operation after adsorption. In addition, compared with the operations such as adsorption, the rectification is high in energy consumption. The target purity may be achieved through one-time rectification by performing adsorption before rectification and performing filtration after rectification, thus avoiding the problem of increased energy consumption caused by multiple rectifications. According to the present invention, production of the acetonitrile with the ultrahigh performance chromatography-mass spectrometry purity is finally realized by using a certain production sequence and controlling parameters therein.

EMBODIMENT

The present invention is described in detail through embodiments. It is necessary to point out herein that the following embodiments are merely intended to further illustrate the present invention and are not construed as limitation to the protection scope of the present invention, and that some non-essential modifications and adaptations made by those skilled in the art according to the above content of the present invention still fall within the protection scope of the present invention.

Embodiment 1

As shown in FIG. 1, the embodiment provides an acetonitrile purification process for an ultrahigh performance liquid chromatography-mass spectrometer, including the following steps:

oxidation: industrial acetonitrile was fed into a reaction kettle 2 through a raw material pump 1, a potassium superoxide composite catalyst was added in the reaction kettle 2, the reaction kettle 2 was heated to obtain gas after reaction was conducted for 1 h under the conditions of 80° C. and 10 kPa, and the obtained gas was condensed by a condenser 3 to enter an intermediate buffer tank 4 to obtain an oxidized material, wherein the preparation raw materials of the potassium superoxide composite catalyst are potassium superoxide, potassium hydroxide and sodium hydroxide with a weight ratio of 1:5:8, and the potassium superoxide composite catalyst accounts for 0.1 wt % of the industrial acetonitrile;

adsorption: the oxidized material sequentially passed through a feeding pump 5 and a flowmeter 6 and was fed into online adsorption columns 7 or regenerative activation columns 8 at a flow velocity of 0.1 m/s to perform cyclic adsorption for 24 h to obtain an absorbed material, wherein the online adsorption columns 7 and the regenerative activation columns 8 are connected in parallel, there are four online adsorption columns 7 and four regenerative activation columns 8, adsorbents of the online adsorption columns 7 and the regenerative activation columns 8 are activated carbon, and a screen size of the activated carbon is 2 mm;

rectification: the adsorbed material was fed into a rectifying kettle 9, phosphorus pentoxide which accounts for 0.1 wt % of the industrial acetonitrile was added into the rectifying kettle 9, the rectifying kettle 9 was heated after reaction was conducted at 80° C. for 1 h, gas in the rectifying kettle 9 was fed into a rectifying tower 10 to perform reflux, of which the flow is 1 kg/h, for 2 h, then gas at the tower top of the rectifying tower 10 was extracted, wherein the extracted flow is 1 kg/h, the extracted reflux ratio is 1:1 and a filler of the rectifying tower 10 is a polytetrafluoroethylene regular filler, the extracted gas sequentially passed through a reflux condenser 11 and a reflux tank 12 to obtain reflux fluid, the initially extracted reflux liquid of 1 h was removed, and the rest reflux fluid was fed into a finished product tank 13 to obtain a semi-finished product; and filtration: the semi-finished product passed through a semi-finished product feeding pump 14 and was sequentially fed into a filter I 15, a filter II 16, a filter III 17, a filter IV 18, a filter V 19 and a filter VI 20 for filtration to obtain acetonitrile for an ultrahigh performance liquid chromatography-mass spectrometer, wherein a filter membrane of the filter I 15 is a polytetrafluoroethylene filter membrane with a pore diameter of 200 nm, filter membranes of the filter II 16 and the filter III 17 are polytetrafluoroethylene sulfonated cationic filter membranes, filter membranes of the filter IV 18 and the filter V 19 are polytetrafluoroethylene anionic filter membranes, and a filter membrane of the filter VI 20 is a polytetrafluoroethylene filter membrane with a pore diameter of 7 nm.

Materials of the reaction kettle 2, the intermediate buffer tank 4, the rectifying kettle 9, the reflux tank 12 and the finished product tank 13 are enamel; and lining materials of the condenser 3, the feeding pump 5, the flowmeter 6, the online adsorption column 7, the regenerative activation column 8, the rectifying tower 10, the reflux condenser 11 and the semi-finished product feeding pump 14 are polytetrafluoroethylene.

The activated carbon is purchased from Shanghai Bilang Environmental Protection Technology Co., Ltd. (the screen size is 2 mm).

The filter membrane of the filter I is a polytetrafluoroethylene fitter membrane which is purchased from Shanghai Bitai Biotechnology Co., Ltd. (the pore diameter is 200 nm).

The polytetrafluoroethylene sulfonated cationic filter membrane is purchased from Hangzhou Aier Environmental Protection Technology Co., Ltd.

The polytetrafluoroethylene anionic filter membrane is purchased from Hangzhou Aier Environmental Protection Technology Co., Ltd.

The filter membrane of the filter VI is a polytetrafluoroethylene filter membrane which is purchased from Shanghai Bitai Biotechnology Co., Ltd. (the pore diameter is 7 nm).

Embodiment 2

As shown in FIG. 1, the embodiment provides an acetonitrile purification process for an ultrahigh liquid chromatography-mass spectrometer, including the following steps:

oxidation: industrial acetonitrile was fed into a reaction kettle 2 through a raw material pump 1, a potassium superoxide composite catalyst was added in the reaction kettle, the reaction kettle 2 was heated to obtain gas after reaction was conducted for 6 h under the conditions of 90° C. and 90 kPa, and the obtained gas was condensed by a condenser 3 to enter an intermediate buffer tank 4 to obtain an oxidized material, wherein the preparation raw materials of the potassium superoxide composite catalyst are potassium superoxide, potassium hydroxide and sodium hydroxide with a weight ratio of 1:5:8, and the potassium superoxide composite catalyst accounts for 5 wt % of the industrial acetonitrile;

adsorption: the oxidized material sequentially passed through a feeding pump 5 and a flowmeter 6 and was fed into online adsorption columns 7 or regenerative activation columns 8 at a flow velocity of 2 m/s to perform cyclic adsorption for 36 h to obtain an absorbed material, wherein the online adsorption columns 7 and the regenerative activation columns 8 are connected in parallel, there are four online adsorption columns 7 and four regenerative activation columns 8, adsorbents of the online adsorption columns 7 and the regenerative activation columns 8 are activated carbon, and a screen size of the activated carbon is 2 mm;

rectification: the adsorbed material was fed into a rectifying kettle 9, phosphorus pentoxide which accounts for 5 wt % of the industrial acetonitrile was added into the rectifying kettle 9, the rectifying kettle 9 was heated after rectification was conducted at 90° C. for 5 h, gas in the rectifying kettle 9 was fed into a rectifying tower 10 to perform reflux, of which the flow is 100 kg/h, for 10 h, then gas at the tower top of the rectifying tower 10 was extracted, wherein the extracted flow is 30 kg/h, the extracted reflux ratio is 2:1 and a tiller of the rectifying tower 10 is a polytetrafluoroethylene regular filler, the extracted gas sequentially passed through a reflux condenser 11 and a reflux tank 12 to obtain reflux fluid, the initially extracted reflux liquid of 5 h was removed, and the rest reflux fluid was fed into a finished product tank 13 to obtain a semi-finished product; and filtration: the semi-finished product passed through a semi-finished product feeding pump 14 and was sequentially fed into a filter I 15, a filter II 16, a filter III 17, a filter IV 18, a filter V 19 and a filter VI 20 for filtration to obtain acetonitrile for an ultrahigh performance liquid chromatography-mass spectrometer, wherein a filter membrane of the filter I 15 is a polytetrafluoroethylene filter membrane with a pore diameter of 200 nm, filter membranes of the filter II 16 and the filter III 17 are polytetrafluoroethylene sulfonated cationic filter membranes, filter membranes of the filter IV 18 and the filter V 19 are polytetrafluoroethylene anionic filter membranes, and a filter membrane of the filter VI 20 is a polytetrafluoroethylene filter membrane with a pore diameter of 7 nm.

Materials of the reaction kettle 2, the intermediate buffer tank 4, the rectifying kettle 9, the reflux tank 12 and the finished product tank 13 are enamel; and lining materials of the condenser 3, the feeding pump 5, the flowmeter 6, the online adsorption column 7, the regenerative activation column 8, the rectifying tower 10, the reflux condenser 11 and the semi-finished product feeding pump 14 are polytetrafluoroethylene.

The activated carbon is purchased from Shanghai Bilang Environmental Protection Technology Co., Ltd. (the screen size is 2 mm).

The filter membrane of the filter I is a polytetrafluoroethylene filter membrane which is purchased from Shanghai Bitai Biotechnology Co., Ltd. (the pore diameter is 200 nm).

The polytetrafluoroethylene sulfonated cationic filter membrane is purchased from Hangzhou Aier Environmental Protection Technology Co., Ltd.

The polytetrafluoroethylene anionic filter membrane is purchased from Hangzhou Aier Environmental Protection Technology Co., Ltd.

The filter membrane of the filter VI is a polytetrafluoroethylene filter membrane which is purchased from Shanghai Bitai Biotechnology Co., Ltd. (the pore diameter is 7 nm).

Embodiment 3

As shown in FIG. 1, the embodiment provides an acetonitrile purification process for an ultrahigh performance liquid chromatography-mass spectrometer, including the following steps:

oxidation: industrial acetonitrile was fed into a reaction kettle 2 through a raw material pump 1, a potassium superoxide composite catalyst was added in the reaction kettle, the reaction kettle 2 was heated to obtain gas after reaction was conducted for 4 h under the conditions of 85° C. and 70 kPa, and the obtained gas was condensed by a condenser 3 to enter an intermediate buffer tank 4 to obtain an oxidized material, wherein the preparation raw materials of the potassium superoxide composite catalyst are potassium superoxide, potassium hydroxide and sodium hydroxide with a weight ratio of 1:5:8, and the potassium superoxide composite catalyst accounts for 0.1 wt % of the industrial acetonitrile;

adsorption: the oxidized material sequentially passed through a feeding pump 5 and a flowmeter 6 and was fed into online adsorption columns 7 or regenerative activation columns 8 at a flow velocity of 1 m/s to perform cyclic adsorption for 30 h to obtain an absorbed material, wherein the online adsorption columns 7 and the regenerative activation columns 8 are connected in parallel, there are four online adsorption columns 7 and four regenerative activation columns 8, adsorbents of the online adsorption columns 7 and the regenerative activation columns 8 are activated carbon, and a screen size of the activated carbon is 2 mm;

rectification: the adsorbed material was fed into a rectifying kettle 9, phosphorus pentoxide which accounts for 0.4 wt % of the industrial acetonitrile was added into the rectifying kettle 9, the rectifying kettle 9 was heated after rectification was conducted at 85° C. for 4 h. gas in the rectifying kettle 9 was fed into a rectifying tower 10 to perform reflux, of which the flow is 70 kg/h, for 7 h, then gas at the tower top of the rectifying tower 10 was extracted, wherein the extracted flow is 20 kg/h, the extracted reflux ratio is 1.5:1 and a filler of the rectifying tower 10 is a polytetrafluoroethylene regular filler, the extracted gas sequentially passed through a reflux condenser 11 and a reflux tank 12 to obtain reflux fluid, the initially extracted reflux liquid of 4 h was removed, and the rest reflux fluid was fed into a finished product tank 13 to obtain a semi-finished product; and filtration: the semi-finished product passed through a semi-finished product feeding pump 14 and was sequentially fed into a filter I 15, a filter II 16, a filter III 17, a filter IV 18, a filter V 19 and a filter VI 20 for filtration to obtain acetonitrile for an ultrahigh liquid chromatography-mass spectrometer, wherein a filter membrane of the filter I 15 is a polytetrafluoroethylene filter membrane with a pore diameter of 200 nm, filter membranes of the filter II 16 and the filter III 17 are polytetrafluoroethylene sulfonated cationic filter membranes, filter membranes of the filter IV 18 and the filter V 19 are polytetrafluoroethylene anionic filter membranes, and a filter membrane of the filter VI 20 is a polytetrafluoroethylene filter membrane with a pore diameter of 7 nm.

Materials of the reaction kettle 2, the intermediate buffer tank 4, the rectifying kettle 9, the reflux tank 12 and the finished product tank 13 are enamel- and lining materials of the condenser 3, the feeding pump 5, the flowmeter 6, the online adsorption column 7, the regenerative activation column 8, the rectifying tower 10, the reflux condenser 11 and the semi-finished product feeding pump 14 are polytetrafluoroethylene.

The activated carbon is purchased from Shanghai Bilang Environmental Protection Technology Co., Ltd. (the screen size is 2 mm).

The filter membrane of the filter I is a polytetrafluoroethylene filter membrane which is purchased from Shanghai Bitai Biotechnology Co., Ltd. (the pore diameter is 200 nm).

The polytetrafluoroethylene sulfonated cationic filter membrane is purchased from Hangzhou Aier Environmental Protection Technology Co., Ltd.

The polytetrafluoroethylene anionic filter membrane is purchased from Hangzhou Aier Environmental Protection Technology Co., Ltd.

The filter membrane of the filter VI is a polytetrafluoroethylene filter membrane which is purchased from Shanghai Bitai Biotechnology Co., Ltd. (the pore diameter is 7 nm).

Embodiment 4

The embodiment provides an acetonitrile purification process for an ultrahigh performance liquid chromatography-mass spectrometer. The specific implementation manner in this embodiment is as same as that in Embodiment 3, except that the activated carbon has a screen size of 4.8 mm and is purchased from Shanghai Bilang Environmental Protection Technology Co., Ltd.

Embodiment 5

The embodiment provides an acetonitrile purification process for an ultrahigh performance liquid chromatography-mass spectrometer. The specific implementation manner in this embodiment is as same as that in Embodiment 3, except that the oxidized material passed through the feeding pump 5 and the flowmeter 6 sequentially and were fed into the online adsorption columns 7 or the regenerative activation columns 8 at a flow velocity of 4 m/s to perform cyclic adsorption for 20 h to obtain the adsorbed material.

Embodiment 6

The embodiment provides an acetonitrile purification process for an ultrahigh performance liquid chromatography-mass spectrometer. The specific implementation manner in this embodiment is as same as that in Embodiment 3, except that there are two online adsorption columns and two regenerative activation columns.

Embodiment 7

The embodiment provides an acetonitrile purification process for an ultrahigh performance liquid chromatography-mass spectrometer. The specific implementation manner in this embodiment is as same as that in Embodiment 3, except that there are five online adsorption columns and five regenerative activation columns.

Embodiment 8

The embodiment provides an acetonitrile purification process for an ultrahigh performance liquid chromatography-mass spectrometer. The specific implementation manner in this embodiment is as same as that in Embodiment 3, except that the adsorbed material was fed into a rectifying kettle 9, phosphorus pentoxide which accounts for 4 wt % of the industrial acetonitrile was added into the rectifying kettle 9, the rectifying kettle 9 was heated after rectification was conducted at 85° C. for 4 h, gas in the rectifying kettle 9 was fed into a rectifying tower 10 to perform reflux, of which the flow is 70 kg/h, for 7 h, then gas in the rectifying tower 10 was extracted, wherein the extracted flow is 20 kg/h, the extracted reflux ratio is 1.5:1 and a filler of the rectifying tower 10 is a polytetrafluoroethylene regular filler, the extracted gas sequentially passed through a reflux condenser 11 and a reflux tank 12 to obtain reflux fluid, and the reflux fluid was fed into a finished product tank 13 to obtain a semi-finished product.

Embodiment 9

The embodiment provides an acetonitrile purification process for an ultrahigh performance liquid chromatography-mass spectrometer. The specific implementation manner in this embodiment is as same as that in Embodiment 3, except that the adsorbed material was fed into a rectifying kettle 9, phosphorus pentoxide which accounts for 0.4 wt % of the industrial acetonitrile was added into the rectifying kettle 9, the rectifying kettle 9 was heated after rectification was conducted at 85° C. for 4 h. gas in the rectifying kettle 9 was fed into a rectifying tower 10 to perform reflux, of which the flow is 70 kg/h, for 7 h, then gas in the rectifying tower 10 was extracted, wherein the extracted flow is 20 kg/h, the extracted reflux ratio is 1.5:1 and a filler of the rectifying tower 10 is a polytetrafluoroethylene regular filler, the extracted gas sequentially passed through a reflux condenser 11 and a reflux tank 12 to obtain reflux fluid, the initially extracted reflux liquid of 6 h was removed, and the rest reflux fluid was fed into a finished product tank 13 to obtain a semi-finished product.

Embodiment 10

The embodiment provides an acetonitrile purification process for an ultrahigh performance liquid chromatography-mass spectrometer. The specific implementation manner in this embodiment is as same as that in Embodiment 3, except that the adsorbed material was fed into a rectifying kettle 9, phosphorus pentoxide which accounts for 0.4 wt % of the industrial acetonitrile was added into the rectifying kettle 9, the rectifying kettle 9 was heated after rectification was conducted at 85° C. for 4 h, gas in the rectifying kettle 9 was fed into a rectifying tower 10 to perform reflux, of which the flow is 140 kg/h, for 7 h, then gas in the rectifying tower 10 was extracted, wherein the extracted flow is 20 k/h, the extracted reflux ratio is 1.5:1 and a filler of the rectifying tower 10 is a polytetrafluoroethylene regular filler, the extracted gas sequentially passed through a reflux condenser 11 and a reflux tank 12 to obtain reflux fluid, the initially extracted reflux liquid of 4 h was removed, and the rest reflux fluid was fed into a finished product tank 13 to obtain a semi-finished product.

Embodiment 11

The embodiment provides an acetonitrile purification process for an ultrahigh liquid chromatography-mass spectrometer. The specific implementation manner in this embodiment is as same as that in Embodiment 3, except that the adsorbed material was fed into a rectifying kettle 9, phosphorus pentoxide which accounts for 0.4 wt % of the industrial acetonitrile was added into the rectifying kettle 9, the rectifying kettle 9 was heated after rectification was conducted at 85° C. for 4 h, gas in the rectifying kettle 9 was fed into a rectifying tower 10 to perform reflux, of which the flow is 70 kg/h, for 7 h, then gas in the rectifying tower 10 was extracted, wherein the extracted flow is 40 kg/h, the extracted reflux ratio is 1.5:1 and a filler of the rectifying tower 10 is a polytetrafluoroethylene regular filler, the extracted gas sequentially passed through a reflux condenser 11 and a reflux tank 12 to obtain reflux fluid, the initially extracted reflux liquid of 4 h was removed, and the rest reflux fluid was fed into a finished product tank 13 to obtain a semi-finished product.

Embodiment 12

The embodiment provides an acetonitrile purification process for an ultrahigh performance liquid chromatography-mass spectrometer. The specific implementation manner in this embodiment is as same as that in Embodiment 3, except that a filter membrane of the filter I 15 is a polyethylene filter membrane with a pore diameter of 200 nm, which is purchased from Hangzhou Aier Environmental Protection Technology Co., Ltd.; and a filter membrane of the filter VI is a polyethylene filter membrane with a pore diameter of 7 nm, which is purchased from Shanghai Bitai Biotechnology Co., Ltd.

Embodiment 13

The embodiment provides an acetonitrile purification process for an ultrahigh performance liquid chromatography-mass spectrometer. The specific implementation manner in this embodiment is as same as that in Embodiment 3, except that filter membranes of the filter II 16 and the filter III 17 are polyether sulfone sulfonated cationic filter membranes, which are purchased from Hangzhou Aier Environmental Protection Technology Co., Ltd.

Embodiment 14

The embodiment provides an acetonitrile purification process for an ultrahigh performance liquid chromatography-mass spectrometer. The specific implementation manner in this embodiment is as same as that in Embodiment 3, except that filter membranes of the filter IV 18 and the filter V 19 are polysulfone anionic filter membranes, which are purchased from Hangzhou Aier Environmental Protection Technology Co., Ltd.

Performance Evaluation

The acetonitrile for the ultrahigh performance liquid chromatography-mass spectrometer prepared by the acetonitrile purification process for the ultrahigh performance liquid chromatography-mass spectrometer, which is provided by the embodiment, serves as a sample to perform the following experiments.

1. Ultraviolet transmittance test: the acetonitrile for the ultrahigh performance liquid chromatography-mass spectrometer provided by the embodiment was subjected to ultraviolet transmittance test of 190-260 nm. The result is shown in Table 1.

TABLE 1

| | Performance characterization test | | | | | | | |
|---|---|---|---|---|---|---|---|---|
| Embodiment | 195 nm | 200 nm | 210 nm | 220 nm | 230 nm | 240 nm | 250 nm | 260 nm |
| 1 | 88.5% | 96.8% | 97.6% | 98.2% | 99.1% | 99.7% | 99.4% | 99.5% |
| 2 | 89.4% | 96.5% | 97.2% | 98.1% | 99.1% | 99.6% | 99.5% | 99.7% |
| 3 | 89.6% | 97.8% | 98.1% | 99.1% | 99.6% | 99.8% | 99.6% | 99.7% |
| 4 | 76.5% | 94.1% | 95.6% | 95.9% | 96.7% | 98.1% | 98.3% | 98.2% |
| 5 | 72.6% | 89.9% | 91.3% | 93.2% | 93.8% | 97.4% | 97.2% | 97.3% |
| 6 | 74.7% | 90.3% | 93.4% | 94.8% | 95.1% | 97.5% | 97.7% | 97.9% |
| 7 | 89.6% | 97.9% | 98.2% | 99.3% | 99.6% | 99.8% | 99.6% | 99.7% |
| 8 | 70.2% | 86.7% | 87.1% | 90.2% | 90.2% | 95.6% | 95.4% | 95.4% |
| 9 | 89.9% | 97.8% | 98.2% | 99.3% | 99.6% | 99.8% | 99.6% | 99.7% |
| 10 | 75.3% | 89.2% | 91.1% | 92.8% | 94.3% | 96.9% | 97.8% | 98.6% |
| 11 | 74.9% | 88.4% | 91.2% | 92.7% | 94.9% | 96.5% | 97.3% | 98.7% |
| 12 | 75.4% | 91.3% | 93.2% | 95.6% | 97.6% | 98.2% | 98.3% | 98.3% |
| 13 | 73.2% | 89.7% | 91.3% | 94.5% | 95.2% | 97.3% | 97.1% | 97.5% |
| 14 | 73.6% | 89.5% | 91.6% | 94.1% | 96.1% | 97.5% | 97.8% | 97.4% |

2. Purity test: the acetonitrile for the ultrahigh performance liquid chromatography-mass spectrometer provided by Embodiment 3 was subjected to purity test of the acetonitrile for the ultrahigh performance liquid chromatography-mass spectrometry, wherein the test standard of the acetonitrile for the ultrahigh performance liquid chromatography-mass spectrometry and the test result of the embodiment are shown in Table 2. It is found that the acetonitrile provided by Embodiment 3 meets the standard of the acetonitrile for the ultrahigh performance liquid chromatography-mass spectrometry. Moreover, the acetonitrile in Embodiments 1-2 was subjected to the above test, and it is also found that the acetonitrile meets the standard. The weight percentage of the acetonitrile for the ultrahigh performance liquid chromatography-mass spectrometer obtained in Embodiments 1-3 in the industrial acetonitrile was calculated to serve as the yield of Embodiments 1-3, it is found that the yield is greater than 95%.

TABLE 2

| Performance characterization test | | | |
|---|---|---|---|
| Detection Items | | Standard Regulation | Embodiment 3 |
| Content | | ≥99.9% | 99.999% |
| Acidity | | ≤0.0002 meq/g | 0.00010 meq/g |
| Alkalinity | | ≤0.0002 meq/g | 0.000025 meq/g |
| Boiling point | | 80-82° C. | 81° C. |
| Chromaticity | | ≤10 APHA | 1 APHA |
| Evaporation residue | | ≤2 ppm | 0.05 ppm |
| Water | | ≤200 ppm | 52.3 ppm |
| Light transmittance | (190 nm) | ≥10% | 38.1% |
| | (195 nm) | ≥80% | 89.6% |
| | (200 nm) | ≥95% | 97.8% |
| | (210 nm) | ≥96% | 98.1% |
| | (220 nm) | ≥97% | 99.1% |
| | (230 nm) | ≥98% | 99.6% |
| | Greater than (240 nm) | ≥99% | 99.8% |
| Gradient (210 nm) | | ≤0.5 mAU | 0.3 mAU |
| Gradient (254 nm) | | ≤0.3 mAU | 0.05 mAU |
| Fluorescence (quinine) 254/365 nm | | ≤0.5 ppb | 0.06 ppb |
| MS-ESI/APCI (as Reserpine negative) | | ≤10 ppb | 3 ppb |
| MS-ESI/APCI (as Reserpine positive) | | ≤2 ppb | 0.7 ppb |
| Al | | <5 ppb | 0.6 ppb |
| Ca | | ≤5 ppb | 1 pb |
| Fe | | ≤5 ppb | 0.2 ppb |
| K | | ≤5 ppb | 2 ppb |
| Mg | | ≤5 ppb | 0.9 ppb |
| Na | | ≤25 ppb | 10 ppb |

Figure 2:
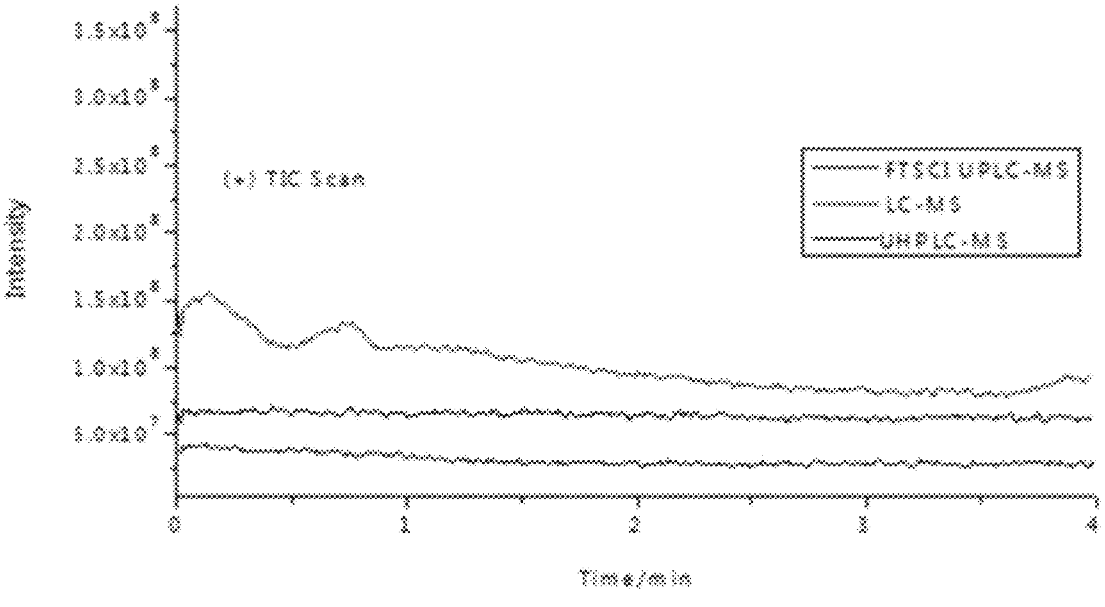
FIG. 2 is a TIC diagram (ESI+) of acetonitrile for an ultrahigh performance liquid chromatography-mass spectrometer (denoted as FT SCI UPLC-MS) provided by Embodiment 3, LS-MS grade acetonitrile of Merck and UHPLC-MS grade acetonitrile.
Figure 3:
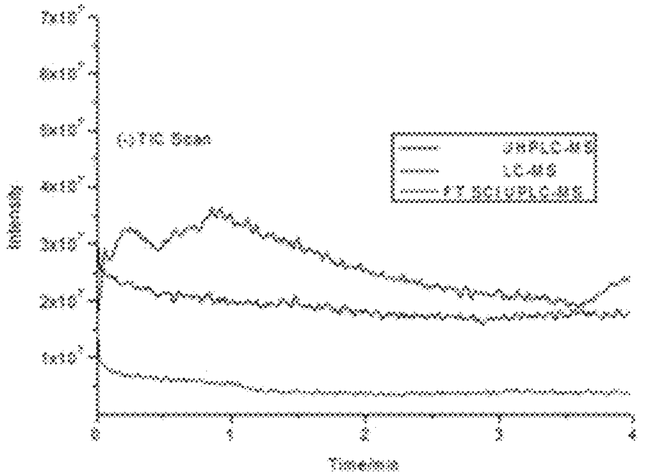
FIG. 3 is a TIC diagram (ESI−) of acetonitrile for an ultrahigh performance liquid chromatography-mass spectrometer (denoted as FT SCI UPLC-MS) provided by Embodiment 3, LS-MS grade acetonitrile of Merck and UHPLC-MS grade acetonitrile.

3. Baseline noise test: the acetonitrile for the ultrahigh performance liquid chromatography-mass spectrometer (denoted as FT SCT UPLC-MS) provided by Embodiment 3, the LC-MS grade acetonitrile of Merck and the UHPLC-MS grade acetonitrile was subjected to LC-MS-MS baseline noise analysis:

test instrument: LCMS-8045;

chromatographic column: Shimpack VP-ODS, 2.0 mm*150 mm;

ion source: ESI/APCI positive and negative mode;

test sample: FT SCI UPLC-MS sample, M brand LC-MS grade sample and M brand UHPLC-MS grade sample;

test method: data was acquired by taking pure acetonitrile as a mobile phase at a flow velocity of 0.5 ml/min and in a Scan mode to obtain diagrams of TIC(ESI+) and TIC (ESI−) respectively, shown in FIG. 2 and FIG. 3, wherein it can be seen from FIG. 2 and FIG. 3 that under the isocratic condition that the mobile phase is pure acetonitrile, the acetonitrile provided by the embodiment has a lower baseline noise value, which shows that the product has lower impurity content.

Figure 4:
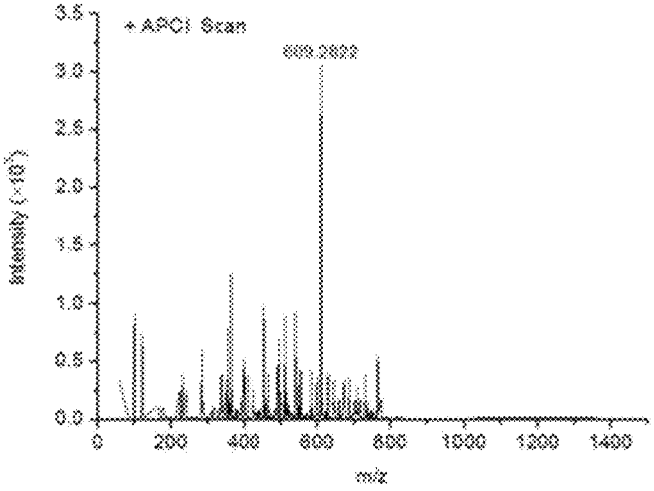
FIG. 4 is a TIC diagram (ESI+) of acetonitrile for an ultrahigh performance liquid chromatography-mass spectrometer (denoted as FT SCI UPLC-MS) provided by Embodiment 3. LS-MS grade acetonitrile and UHPLC-MS grade acetonitrile.
Figure 5:
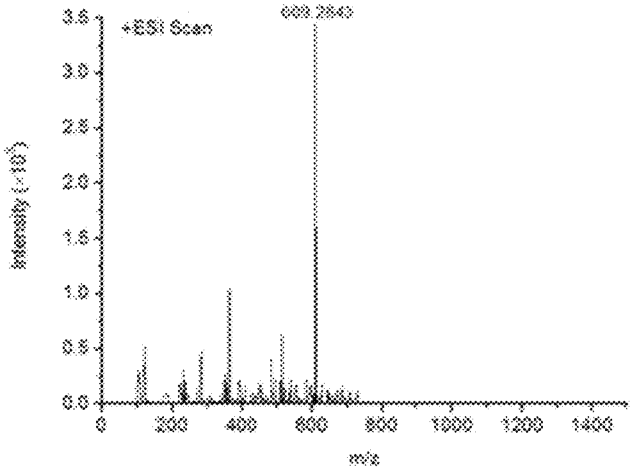
FIG. 5 is a Q-TOF LCMS Reserpine mass spectrogram (Scan, ESI+) of acetonitrile for an ultrahigh performance liquid chromatography-mass spectrometer provided by Embodiment 3.

4. Adaptability analysis: the acetonitrile for the ultrahigh performance liquid chromatography-mass spectrometer provided by Embodiment 3 was subjected to adaptability analysis:

test instrument: Agilent 1260+6530 Q-TOF LCMS;

chromatographic column: Waters ACQUITY UPLC BEH C18, 2.1×100 mm, 1.7 μm;

ion source: ESI/APCI positive and negative ions;

Reserpine standard solution: dissolved and prepared corresponding to the test acetonitrile sample; and test method: LC gradient condition: 0-0.5 min, 20% acetonitrile, 0.5-2.0 min, 100% acetonitrile, 2.0-5.0 min, 100% acetonitrile, 5.0-8.0 min, 20% acetonitrile, flow velocity: 0.5 mL/min. 2 ppb reserpine standard solution was sampled, and data was acquired in a Scan mode to obtain the Q-TOF LCMS reserpine mass spectrogram (Scan, APCI+) (FIG. 4) and Q-TOF LCMS reserpine mass spectrogram (Scan, ESI+) (FIG. 5). It can be seen from FIG. 4 and FIG. 5 that under the same Scan mode and the gradient condition, after the reserpine sample standard solution was sampled, through comparison, it can be obviously seen that the mass spectrometric peak intensity of all other baseline impurities is less than the molecular ion peak of the 2 ppb reserpine (m/z 609.2843), which fully indicates that the FT SCI UPLC-MS grade solvent has extremely low impurity content and impurity interference peak, thus ensuring extremely low solvent inhibition effect and maximizing the analysis sensitivity.

It can be seen from the test results of Tables 2-3 and FIG. 2 to FIG. 5 that by the acetonitrile purification process provided by the present invention, acetonitrile with ultrahigh performance liquid chromatography-mass spectrometry purity may be obtained and the yield is more than 95%. In addition, it can be seen from the baseline noise test and the adaptability analysis that compared with existing products, the acetonitrile prepared by the purification process provided by the present invention has lower impurity content, thus avoiding the influence on the sensitivity of the ultrahigh performance liquid chromatography-mass spectrometer.

The foregoing examples are merely illustrative and are used to explain some features of the method according to the present invention. The appended claims are intended to claim the conceivable scope as broad as possible, and the embodiments presented herein are illustrative only of implementation selected in accordance with a combination of all possible embodiments. Therefore, the intention of the applicant is that the appended claims will not be limited by the choice of the embodiments illustrating the features of the present invention. Some numerical ranges used in the claims are also inclusive of subranges therein and variations in these ranges should also be interpreted as being covered by the appended claims where possible.

What is claimed is:

1. An acetonitrile purification process, comprising the following steps:

oxidation: feeding industrial acetonitrile into a reaction kettle through a raw material pump, adding a catalyst in the reaction kettle, heating the reaction kettle after reacting for 1 to 6 h under the conditions of 80 to 90° C. and 10 to 90 kPa, and condensing the obtained gas by a condenser to enter an intermediate buffer tank to obtain an oxidized material;

adsorption: feeding the oxidized material into an adsorption column through a feeding pump and a flowmeter sequentially, and performing adsorption at a flow velocity of 0.01 to 2 m/s to obtain an absorbed material; wherein the adsorption column comprises an online adsorption column and a regenerative activation column which are connected in parallel;

rectification: feeding the adsorbed material into a rectifying kettle, adding a drying agent into the rectifying kettle, heating the rectifying tower after reacting at 80 to 90° C. for 1 to 5 h, feeding gas generated in the rectifying tower into a rectifying tower to perform reflux for 2 to 10 h, extracting a tower top gas of the rectifying tower, removing the initially extracted reflux fluid of 1 to 5 h, and the rest of the reflux fluid being sequentially pass through a reflux condenser and a reflux tank, and feeding the obtained reflux fluid into a finished product tank to obtain a semi-finished product; wherein the flow of the reflux is 1 to 100 kg/h; the extracted flow is 1-30 kg/h, and the extracted reflux ratio is (1-2):1; and filtration: filtering the semi-finished product to obtain acetonitrile for an ultrahigh performance liquid chromatography-mass spectrometer, wherein the regenerative activation columns and the online adsorption columns have the same quantity, and there is 1, 2, 3, 4, or 5 online adsorption columns.

2. The acetonitrile purification process according to claim 1, wherein the catalyst accounts for 0.01 to 5 wt % of the industrial acetonitrile.

3. The acetonitrile purification process according to claim 1, wherein in the filtration, the semi-finished product is sequentially filtered by a first filter, a second filter, a third filter, a fourth filter, a fifth filter and a sixth filter to obtain acetonitrile for the ultrahigh performance liquid chromatography-mass spectrometer.

4. The acetonitrile purification process according to claim 3, wherein the type of a filter membrane of the filter is selected from two or more of a plastic filter membrane, an anionic filter membrane and a cationic filter membrane.

* * * * *